United States Patent
Shigenobu et al.

(10) Patent No.: US 6,632,935 B2
(45) Date of Patent: Oct. 14, 2003

(54) GENOME DNA OF BACTERIAL SYMBIONT OF APHIDS

(75) Inventors: Shuji Shigenobu, Tokyo (JP); Hidemi Watanabe, Kanagawa (JP); Hajime Ishikawa, Kanagawa (JP); Masahira Hattori, Tokyo (JP); Yoshiyuki Sakaki, Kanagawa (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 09/790,988

(22) Filed: Feb. 23, 2001

(65) Prior Publication Data

US 2002/0127687 A1 Sep. 12, 2002

(30) Foreign Application Priority Data

Apr. 7, 2000 (JP) ........................................ 2000-107160

(51) Int. Cl.⁷ .................. C07H 21/04; C07H 21/00; G12P 21/02; C12N 1/20
(52) U.S. Cl. .................... 536/23.1; 536/22.1; 536/23.2; 536/24.5; 536/23.7; 435/24.3; 435/317.1; 435/346; 435/418; 435/419; 435/69.5; 435/253.2; 435/253.6
(58) Field of Search .............................. 536/22.1, 23.7, 536/23.2, 24.5, 23.1; 435/24.3, 317.1, 346, 418–419, 69.5, 253.2–253.6

(56) References Cited

U.S. PATENT DOCUMENTS 5,817,479 A 10/1998 Au-Young et al.
6,020,165 A 2/2000 Yue et al.
6,051,424 A 4/2000 Kato et al.

OTHER PUBLICATIONS

Ohtaka et al 1993 J. Molecular Evolution 1993, 36 (2), 121–126.*
Sato et al 1997, J. Bacteriology , 179, 2300–2304.*
Matsumoto et al 1999, J. BioChem, 126; 578–583.*
Brochure of Kodon™, http://www.applied–maths.com/download/folder_kodon.doc, 2002 Total Genome and Sequence Audyn's Software, 2 pgs.
Nippon Nogeikagaku Kaishi, Journal of the Japan Society for Bioscience, Biotechnology, and Agrochemistry, issued Feb. 25,2000 with English translation.
S. Shigenobu et al., Genome sequence of the endocellular bacterial symbiont of aphids Buchnera sp. APS, Nature, vol. 407, No. 6800, pp. 81–86 (Sep. 7, 2000).

* cited by examiner

Primary Examiner—Lynette R. F. Smith
Assistant Examiner—Padmavathi Baskar
(74) Attorney, Agent, or Firm—Foley & Lardner

(57) ABSTRACT

The present invention provides a genomic DNA of Buchnera. That is, this invention provides genes derived from Buchnera sp., comprising DNA of the following (a) or (b);
(a) a DNA selected from a group consisting of a DNA having a nucleotide sequence ranging from a start point to an end point as shown in Table 1 in a nucleotide sequence represented by SEQ ID NO:1, or a DNA complementary thereto, and
(b) a DNA hybridizing to the DNA of (a) under stringent conditions and encoding a protein having a function same as that of the product expressed by the DNA.

1 Claim, 1 Drawing Sheet

GENOME DNA OF BACTERIAL SYMBIONT OF APHIDS

FIELD OF THE INVENTION

The present invention relates to genomic DNA and plasmid DNA of aphids Buchnera sp.

BACKGROUND OF THE INVENTION

Buchnera sp. APS is a bacterial symbiont harbored by aphids. The host aphids are insects belonging to the suborder homoptero of the order hemiptera. Nearly 10,000 species of them are known throughout the world. Aphids have extremely strong fertility based on diploid parthenogenesis, and are one of the most serious agricultural insect pests on the earth. Aphids harbor many bacteria called Buchnera sp. in specialized cells, called bacteriocyte. The mutualism between Buchnera and aphids is so obligate that the symbiont Buchnera cannot survive outside the host aphid and aphids lacking Buchnera lose their fertility in addition to decreased growth.

Hence, noticing the host-symbiont relationship of the aphid and Buchnera is useful to obtain information to destroy aphids.

SUMMARY OF THE INVENTION

The present invention is to provide genomic DNA and plasmid DNA of Buchnera sp.

The present inventors have succeeded in determining a whole nucleotide sequence of genome of Buchnera, which is a bacterial symbiont harbored by Acyrthosiphon pisum and in identifying 619 genes (including plasmids) contained in the genome as a result of diligent research on the above problems.

That is, the present invention provides genes derived from Buchnera sp., comprising DNA of (a) or (b) as follows.

(a) a DNA selected from a group consisting of a DNA having a nucleotide sequence ranging from a start point to an end point as shown in Table 1 in a nucleotide sequence represented by SEQ ID NO:1, or a DNA complementary thereto, and (b) a DNA hybridizing to said DNA of (a) under stringent conditions and encoding a protein having a function same as that of the product expressed by the DNA.

Here, the term "the product expressed by said DNA" means one of (a substance encoded by a sequence ranging from a start point to an end point) substances described in "Substance Name" column of Table 1.

Further, the present invention provides a recombinant vector containing the above gene or a transformant containing the vector.

Furthermore, the present invention provides genomic DNA of Buchnera sp. having a nucleotide sequence represented by SEQ ID NO:1.

Furthermore, the present invention provides a plasmid derived from Buchnera sp., comprising DNA of the (c) or (d) as follows.

(c) a DNA having a nucleotide sequence represented by SEQ ID NO:2 or 3, and (d) a plasmid, capable of hybridizing to the DNA having a nucleotide sequence represented by SEQ ID NO:2 or 3 under stringent conditions, and self-replicating.

Further, the present invention provides a method of producing the above-mentioned protein, comprising the steps of culturing the transformant and collecting the protein expressed by a target gene from the resulting culture product.

Hereinafter, a more detailed explanation of this invention will be given. The present specification includes the contents of the specifications and/or drawings of the Japanese Patent Applications No. 2000-107160 based on which the present application claims priority.

The present invention relates to genomic DNA with a length of approximately 640 kb of Buchnera sp. (hereinafter also referred to as Buchnera) and two plasmid DNAs present in Buchnera sp.

1. Cloning of Buchnera genomic DNA and plasmids

Buchnera can be obtained by the following techniques. For example, the host aphids harboring Buchnera are dissected, and huge cells (called bacteriocyte) in which Buchnera is living are isolated. The bacteriocytes are crushed and filtered through a 5 μm pore size filter, thereby isolating Buchnera. Buchnera can also be isolated by homogenizing aphids and filtering the homogenates through 20, 10, and 5 μm pore size filters in order. Moreover, Buchnera can be isolated by density gradient centrifugation using sucrose or percoll (Pharmacia).

An example of aphids is Acyrthosiphon pisum (Harris).

Next, genomic DNA is prepared from Buchnera. The genomic DNA can be prepared by known methods including a phenol/chloroform protocol.

Thus obtained DNA can be analyzed by the whole genome shotgun sequencing in this invention. The whole genome shotgun sequencing is to provide information on a whole genomic sequence, comprising the steps of fragmenting and sequencing randomly the whole genome in large quantities, and searching fragment ends overlapping to each other using a computer to join them together. That is, this method involves sequencing each DNA fragment treated with restriction enzymes or each DNA fragment fragmented at a random site using HydroShear (GeneMachines) and the like, comparing the sequences to each other to find overlapping portions, and then connecting the overlapping ends of the fragments, whereby determining the whole sequence.

This technique is basically the same as that of Fleischmann R. D. et al (Whole-genome random sequencing and assembly of Haemophilus influenzae Rd. Science 269, 469–512, 1995). In order to avoid chimera formation in preparing shotgun sequence libraries, some methods (for example, Partial Fill-in method) can be adapted. In the partial fill-in method, bases of overhang ends are partially polymerized.

The nucleotide sequences of the above DNA fragments can be determined by known techniques including Sanger method (Molecular Cloning, vol. 2, 13.3, 1989) and methods based on PCR. Normally, nucleotide sequences are determined by performing sequencing reactions with PRISM sequencing kit and the like containing fluorescent dideoxy terminator (Perkin Elmer), and using an autosequencer (model ABI 377, Applied Biosystem).

SEQ ID NO:1 represents the whole sequence of the genomic DNA of this invention. In addition, Table 1 shows all the genes (608 genes excluding plasmids) contained in the nucleotide sequence of the chromosome represented by SEQ ID NO:1. 572 genes encoding proteins contained in the above genes can be isolated by, for example, PCR method. In Table 1, "F" represents + chain and "R" represents − chain in the data in "Orientation" column. "Type" represents the sequence type of a gene. For example, CDS represents translation regions for proteins, tRNA transfer RNA, rRNA ribosomal RNA, and PS pseudogenes. Pseudogenes (PS) contain frameshift mutation or a stop codon inserted in the middle. When a direction is "F," data in "Start point" column represents an initiation point for translation of a substance to be encoded by the gene, and data in "End point" column represents a termination point for the translation. For example, in Table 1, a second (BU002) gene (gene name: atpB) corresponds to a nucleotide sequence from $2278^{th}$ to $3102^{nd}$ bases and encodes ATP-synthetase A-chain. When a direction is "R," translation proceeds in the direction opposite to that of the complementary strand from an initiation to an end point. For example, in Table 1, a $10^{th}$ (BU010) gene (gene name: gyrB) represents a complementary strand of a nucleotide sequence from $8911^{th}$ to $11322^{nd}$ bases of a nucleotide sequence of SEQ ID NO:1. Translation proceeds in the direction from $11322^{nd}$ to $8911^{th}$ base based on the sequence position in SEQ ID NO:1. The remainder genes also encode substances (proteins, enzymes nucleic acids and the like) described in "Substance name" column according to nucleotide sequences between "Start point" and "End point" described in Table 1 or their complementary sequences.

TABLE 1

| ID | gene name | type[a] | orientation | start (bp) | end (bp) | description |
|---|---|---|---|---|---|---|
| BU001 | gidA | CDS | F | 197 | 2083 | glucose inhibited division protein A |
| BU002 | atpB | CDS | F | 2278 | 3102 | ATP synthase A chain |
| BU003 | atpE | CDS | F | 3139 | 3378 | ATP synthase C chain |
| BU004 | atpF | CDS | F | 3497 | 3982 | ATP synthase B chain |
| BU005 | atpH | CDS | F | 3982 | 4515 | ATP synthase delta chain |
| BU006 | atpA | CDS | F | 4530 | 6068 | ATP synthase alpha chain |
| BU007 | atpG | CDS | F | 6101 | 6973 | ATP synthase gamma chain |
| BU008 | atpD | CDS | F | 6997 | 8394 | ATP synthase beta chain |
| BU009 | atpC | CDS | F | 8421 | 8837 | ATP synthase epsilon chain |
| BU010 | gyrB | CDS | R | 8911 | 11322 | DNA gyrase subunit B |
| BU011 | dnaN | CDS | R | 11449 | 12549 | DNA polymerase III beta chain |
| BU012 | dnaA | CDS | R | 12554 | 13918 | chromosomal replication initiator protein dnaA |
| BU013 | rpmH | CDS | F | 14369 | 14512 | 50S ribosomal protein L34 |
| BU014 | rnpA | CDS | F | 14525 | 14872 | ribonuclease P protein component |
| BU015 | yidC | CDS | F | 15011 | 16609 | 60 kD inner-membrane protein |
| BU016 | thdF | CDS | F | 16651 | 18009 | thiophene and furan oxidation protein thdF |
| BU017 | tRNA-Phe | tRNA | R | 18028 | 18100 | tRNA-Phe (GAA) |
| BU018 | mopB | CDS | F | 18376 | 18666 | 10 kD chaperonin |
| BU019 | mopA | CDS | F | 18715 | 20361 | 60 kD chaperonin |
| BU020 | efp | CDS | F | 20985 | 21596 | elongation factor P |
| BU021 | dnaC | CDS | R | 21614 | 22354 | DNA replication protein dnaC |
| BU022 | dnaT | CDS | R | 22354 | 22848 | primosomal protein I |
| BU023 | yhhF | CDS | R | 22945 | 23520 | hypothetical protein |
| BU024 | ftsY | CDS | F | 23651 | 24787 | cell division protein ftsY |
| BU025 | rpoH | CDS | F | 24950 | 25804 | RNA polymerase sigma-32 factor |
| BU026 | glmS | CDS | R | 25945 | 27810 | D-fructose-6-phosphate amidotransferase |
| BU027 | glmU | CDS | R | 27844 | 29223 | UDP-N-acetylglucosamine pyrophosphorylase |
| BU028 | yigL | CDS | F | 29403 | 29972 | hypothetical protein |
| BU029 | cof | CDS | F | 30011 | 30220 | cof protein |
| BU030 | metE | CDS | F | 31191 | 33467 | 5-methyltetrahydropteroyltriglutamate-homocysteine S-methyltransferase |
| BU031 | purH | CDS | R | 33590 | 35167 | phosphoribosylaminoimidazolecarboxamide formyltransferase/IMP cyclohydrolase |
| BU032 | hupA | CDS | R | 35308 | 35586 | DNA-binding protein hu-alpha |
| BU033 | rpoC | CDS | R | 36321 | 40544 | DNA-directed RNA polymerase beta' chain |
| BU034 | rpoB | CDS | R | 40622 | 44650 | DNA-directed RNA polymerase beta chain |
| BU035 | rplL | CDS | R | 44871 | 45239 | 50S ribosomal protein L7/L12 |
| BU036 | rplJ | CDS | R | 45306 | 45803 | 50S ribosomal protein L10 |
| BU037 | rplA | CDS | R | 46069 | 46764 | 50S ribosomal protein L1 |
| BU038 | rplK | CDS | R | 46767 | 47195 | 50S ribosomal protein L11 |
| BU039 | nusG | CDS | R | 47243 | 47788 | transcription antitermination protein nusG |
| BU040 | secE | CDS | R | 47791 | 48174 | preprotein translocase secE subunit |
| BU041 | tRNA-Thr | tRNA | R | 48488 | 48560 | tRNA-Thr (GGT) |
| BU042 | tRNA-Gly | tRNA | R | 48576 | 48647 | tRNA-Gly (TCC) |
| BU043 | tRNA-Tyr | tRNA | R | 48670 | 48754 | tRNA-Tyr (GTA) |
| BU044 | tRNA-Thr | tRNA | A | 48770 | 48842 | tRNA-Thr (TGT) |
| BU045 | murB | CDS | R | 48981 | 50051 | UDP-N-acetylenolpyruvoylglucosamine reductase |
| BU046 | metF | CDS | F | 50166 | 51044 | 5,10-methylenetetrahydrofolate reductase |
| BU047 | argE | CDS | R | 51056 | 52201 | acetylornithine deacetylase |
| BU048 | argC | CDS | F | 52362 | 53366 | N-acetyl-gamma-glutamyl-phosphate reductase |
| BU049 | argB | CDS | F | 53387 | 54160 | acetylglutamate kinase |
| BU050 | argG | CDS | F | 54190 | 55401 | argininosuccinate synthase |
| BU051 | argH | CDS | F | 55473 | 56852 | argininosuccinate lyase |
| BU052 | yibN | CDS | F | 56934 | 57368 | hypothetical protein |
| BU053 | secB | CDS | F | 57475 | 57903 | protein-export protein secB |
| BU054 | cysE | CDS | F | 58005 | 58829 | serine acetyltransferase |
| BU055 | rpoD | CDS | R | 58935 | 60773 | ANA polymerase sigma factor rpoD |
| BU056 | dnaG | CDS | R | 60941 | 62674 | DNA primase |
| BU057 | rpsU | CDS | R | 62755 | 62970 | 30D ribosomal protein S21 |
| BU058 | vgjD | CDS | F | 63204 | 64214 | O-sialoglycoprotein endopeptidase |
| BU059 | ribB | CDS | R | 64192 | 64839 | 3,4-dihydroxy-2-butanone 4-phosphate synthase |
| BU060 | yb3052 | CDS | R | 65111 | 66058 | putative kinase |
| BU061 | cca | CDS | F | 66272 | 67516 | tRNA nucleotidyltransferase |
| BU062 | bacA | CDS | R | 67542 | 68339 | bacitracin resistance protein |
| BU063 | crr | CDS | R | 68425 | 68910 | glucose-permease IIA component |
| BU064 | ptsI | CDS | R | 68960 | 70675 | phosphoenolpyruvate-protein phosphotransferase |
| BU065 | ptsH | CDS | R | 70824 | 71081 | phosphocarrier protein HPr |
| BU066 | cysK | CDS | R | 71230 | 72177 | cysteine synthase A |

TABLE 1-continued

| ID | gene name | type[a] | orientation | start (bp) | end (bp) | description |
|---|---|---|---|---|---|---|
| BU067 | lig | CDS | F | 72432 | 74459 | DNA ligase (NAD+) |
| BU068 | tRNA-Lys | tRNA | R | 74471 | 74543 | tRNA-Lys (TTT) |
| BU069 | tRNA-Val | tRNA | R | 74572 | 74644 | tRNA-Val (TAC) |
| BU070 | gltX | CDS | F | 74771 | 76174 | glutamyl-tRNA synthetase |
| BU071 | tRNA-Ala | tRNA | F | 76347 | 76422 | tRNA-Ala (GGC) |
| BU072 | fliE | CDS | R | 76514 | 76810 | flagellar hook-basal body complex protein fliE |
| BU073 | fliF | CDS | F | 77074 | 78711 | flagellar M-ring protein |
| BU074 | fliG | CDS | F | 78708 | 79703 | flagellar motor switch protein fliG |
| BU075 | fliH | CDS | F | 79696 | 80358 | flagellar assembly protein fliH |
| BU076 | fliI | CDS | F | 80316 | 81719 | flagellum-specific ATP synthase |
| BU077 | fliJ | CDS | F | 81749 | 82186 | flagehlar fliJ protein |
| BU078 | yba2 | CDS | F | 82195 | 82533 | hypothetical protein |
| BU079 | fliK | CDS | F | 82624 | 83331 | flagellar hook-length control protein |
| BU080 | fliM | CDS | F | 83392 | 84339 | flagellar motor switch protein fliM |
| BU081 | fliN | CDS | F | 84332 | 84733 | flagellar motor switch protein fliN |
| BU082 | fliP | CDS | F | 84745 | 85884 | flagellar biosynthetic protein fliP |
| BU083 | fliQ | CDS | F | 85956 | 86225 | flagellar biosynthetic protein fliQ |
| BU084 | fliR | CDS | F | 86225 | 87001 | flagellar biosynthetic protein fliR |
| BU085 | rpmG | CDS | R | 87154 | 87321 | 50S ribosomal protein L33 |
| BU086 | rpmB | CDS | R | 87332 | 87559 | 50S ribosomal protein L28 |
| BU087 | ytfN | CDS | F | 87905 | 90817 | hypothetical protein |
| BU088 | ppa | CDS | R | 90833 | 91381 | inorganic pyrophosphatase |
| BU089 | pmbA | CDS | F | 91575 | 92915 | pmbA protein |
| BU090 | rnpB | RNA | R | 92990 | 93313 | ribonuclease P RNA component |
| BU091 | yraL | CDS | R | 93393 | 94241 | hypothetical protein |
| BU092 | fabB | CDS | F | 94380 | 95600 | 3-oxoacyl-[acyl-carrier-protein] synthase I |
| BU093 | talA | CDS | F | 95840 | 96790 | transaldolase A |
| BU094 | tktB | CDS | F | 96845 | 98842 | transketolase |
| BU095 | dapE | CDS | F | 98947 | 100074 | succinyl-diaminopimelate desuccinylase |
| BU096 | dapA | CDS | R | 100464 | 101348 | dihydrodipicolinate synthase |
| BU097 | aroC | CDS | R | 101924 | 102988 | chorismate synthase |
| BU098 | yb2331 | CDS | F | 103284 | 103844 | hypothetical protein |
| BU099 | hisG | CDS | F | 104169 | 105068 | ATP phosphoribosyltransferase |
| BU100 | hisD | CDS | F | 105077 | 106384 | histidinol dehydrogenase |
| BU101 | hisC | CDS | F | 106381 | 107487 | histidinol-phosphate aminotransferase |
| BU102 | hisB | CDS | F | 107477 | 108538 | imidazoleglycerol-phosphate dehydratase/histidinol-phosphatase |
| BU103 | hisH | CDS | F | 108538 | 109128 | amidotransferase hisH |
| BU104 | hisA | CDS | F | 109133 | 109873 | phosphoribosylformimino-5-aminoimidazole carboxamide ribotide isomerase |
| BU105 | hisF | CDS | F | 109852 | 110628 | hisF protein |
| BU106 | hisI | CDS | F | 110622 | 111269 | phosphoribosyl-AMP cyclohydrolase/phosphoribosyl-ATP pyrophosphohydrolase |
| BU107 | gnd | CDS | F | 111628 | 113034 | 6-phosphogluconate dehydrogenase (decarboxylating) |
| BU108 | dcd | CDS | F | 113197 | 113817 | deoxycytidine triphosphate deaminase |
| BU109 | metG | CDS | F | 113965 | 115608 | methionyl-tRNA synthetase |
| BU110 | mesJ | CDS | R | 115656 | 116978 | cell cycle protein mesJ |
| BU111 | tRNA-Val | tRNA | R | 117007 | 117080 | tRNA-Val (GAC) |
| BU112 | ribE | CDS | F | 117204 | 117830 | riboflavin synthase alpha chain |
| BU113 | rnfA | CDS | F | 117867 | 118445 | hypothetical protein |
| BU114 | rnfB | CDS | F | 118451 | 118954 | Ferredoxin II |
| BU115 | rnfC | CDS | F | 119117 | 120538 | putative membrane protein |
| BU116 | ydgO | CDS | F | 120631 | 121629 | hypothetical protein |
| BU117 | rnfG | CDS | F | 121778 | 122272 | nitrogen fixation protein |
| BU118 | ydgQ | CDS | F | 122247 | 122930 | hypothetical protein |
| BU119 | nth | CDS | F | 122941 | 123573 | endonuclease III |
| BU120 | priA | CDS | F | 123653 | 125776 | primosomal protein N |
| BU121 | tyrS | CDS | F | 125936 | 127204 | tyrosyl-tRNA synthetase |
| BU122 | vdiC | CDS | R | 127212 | 127604 | hypothetical protein |
| BU123 | yb1688 | CDS | F | 127828 | 128910 | hypothetical protein |
| BU124 | aroH | CDS | F | 129262 | 130308 | phospho-2-dehydro-3-deoxyheptonate aldolase (Trp-sensitive) |
| BU125 | thrS | CDS | F | 130460 | 132388 | threonyl-tRNA synthetase |
| BU126 | infC | CDS | F | 132392 | 132931 | translation initiation factor IF-3 |
| BU127 | rpmI | CDS | F | 133018 | 133215 | 50S ribosomal protein L35 |
| BU128 | rplT | CDS | F | 133258 | 133614 | 50S ribosomal protein L20 |
| BU129 | pheS | CDS | F | 133809 | 134798 | phenylalanyl-tRNA synthetase alpha chain |
| BU130 | pheT | CDS | F | 134808 | 137195 | phenylalanyl-tRNA synthetase beta chain |
| BU131 | himA | CDS | F | 137200 | 137508 | integration host factor alpha-subunit |
| BU132 | queA | CDS | F | 137550 | 138623 | S-adenosylmethionine:tRNA ribosyltransferase-isomerase |
| BU133 | tgt | CDS | F | 138664 | 139776 | queuine tRNA-ribosyltransferase |
| BU134 | yajC | CDS | F | 139801 | 140136 | hypothetical protein |
| BU135 | glyS | CDS | R | 140188 | 142260 | glycyl-tRNA synthetase beta chain |
| BU136 | glyQ | CDS | R | 142235 | 143203 | glycyl-tRNA synthetase alpha chain |
| BU137 | nfo | CDS | F | 143868 | 144713 | endonuclease IV |

TABLE 1-continued

| ID | gene name | type[a] | orientation | start (bp) | end (bp) | description |
|---|---|---|---|---|---|---|
| BU138 | rplY | CDS | F | 144748 | 145035 | 50S ribosomal protein L25 |
| BU139 | yabI | CDS | R | 145105 | 145875 | hypothetical protein |
| BU140 | surA | CDS | F | 146062 | 147354 | survival protein surA precursor |
| BU141 | ksgA | CDS | F | 147408 | 148229 | dimethyladenosine transferase |
| BU142 | apaH | CDS | F | 148274 | 149066 | bis(5'-nucleosyl)-tetraphosphatase (symmetrical) |
| BU143 | folA | CDS | R | 149125 | 149610 | dihydrofolate reductase |
| BU144 | carB | CDS | R | 149700 | 152939 | carbamoyl-phosphate synthase large chain |
| BU145 | carA | CDS | R | 152953 | 154116 | carbamoyl-phosphate synthase small chain |
| BU146 | dapB | CDS | R | 154326 | 155135 | dihydrodipicolinate reductase |
| BU147 | lytB | CDS | R | 155139 | 156098 | lytB protein |
| BU148 | lspA | CDS | R | 156163 | 156645 | lipoprotein signal peptidase |
| BU149 | ileS | CDS | R | 156645 | 159467 | isoleucyl-tRNA synthetase |
| BU150 | ribF | CDS | R | 159484 | 160425 | riboflavin kinase/FMN adenylyltransferase |
| BU151 | rpsT | CDS | F | 180640 | 160909 | 30S ribosomal protein S20 |
| BU152 | dnaJ | CDS | R | 160960 | 162093 | dnaJ protein |
| BU153 | dnaK | CDS | R | 162206 | 164119 | dnaK protein |
| BU154 | nuoA | CDS | F | 164454 | 164858 | NADH dehydrogenase I chain A |
| BU155 | nuoB | CDS | F | 164892 | 165566 | NADH dehydrogenase I chain B |
| BU156 | nuoCD | CDS | F | 165657 | 167459 | NADH dehydrogenase I chain C/D |
| BU157 | nuoE | CDS | F | 167482 | 167970 | NADH dehydrogenase I chain E |
| BU158 | nuoF | CDS | F | 167967 | 169301 | NADH dehydrogenase I chain F |
| BU159 | nuoG | CDS | F | 169395 | 172115 | NADH dehydrogenase I chain G |
| BU160 | nuoH | CDS | F | 172127 | 173095 | NADH dehydrogenase I chain H |
| BU161 | nuoI | CDS | F | 173120 | 173662 | NADH dehydrogenase I chain I |
| BU162 | nuoJ | CDS | F | 173672 | 174184 | NADH dehydrogenase I chain J |
| BU163 | nuoK | CDS | F | 174215 | 174517 | NADH dehydrogenase I chain K |
| BU164 | nuoL | CDS | F | 174514 | 176358 | NADH dehydrogenase I chain L |
| BU165 | nuoM | CDS | F | 176455 | 177972 | NADH dehydrogenase I chain M |
| BU166 | nuaN | CDS | F | 178030 | 179439 | NADH dehydrogenase I chain N |
| BU167 | folC | CDS | F | 180565 | 181800 | folylpolyglutamate synthase/dihydrofolate synthase |
| BU168 | cvpA | PS | F | 181820 | 182301 | colicin V production protein with frameshift |
| BU169 | prsA | CDS | R | 182379 | 183317 | ribose-phosphate pyrophosphokinase |
| BU170 | ychB | CDS | R | 183446 | 184330 | hypothetical protein |
| BU171 | prfA | CDS | F | 184538 | 185623 | peptide chain release factor 1 |
| BU172 | hemK | CDS | F | 185620 | 186453 | hemK protein |
| BU173 | ychA | CDS | F | 186613 | 187422 | hypothetical protein |
| BU174 | nadE | CDS | R | 187430 | 188236 | nh(3)-dependent NAO(+) synthetase |
| BU175 | ackA | CDS | F | 188320 | 189537 | acetate kinase |
| BU176 | pta | CDS | F | 189582 | 191708 | phosphate acetyltransferase |
| BU177 | yfaE | CDS | R | 191740 | 192003 | hypothetical protein |
| BU178 | nrdB | CDS | R | 192006 | 193136 | ribonucleoside-diphosphate reductase 1 beta chain |
| BU179 | nrdA | CDS | R | 193204 | 195489 | ribonucleoside-diphosphate reductase 1 alpha chain |
| BU180 | gyrA | CDS | R | 195562 | 198054 | DNA gyrase subunit A |
| BU181 | yba2 | CDS | F | 198321 | 199037 | hypothetical protein |
| BU182 | ahpC | CDS | R | 199160 | 199753 | alkyl hydroperoxide reductase |
| BU183 | ung | CDS | F | 199831 | 200493 | uracil-DNA glycosylase |
| BU184 | grpE | CDS | R | 200569 | 201135 | heat shock protein grpE 2 |
| BU185 | yfjB | CDS | F | 201252 | 202130 | hypothetical protein |
| BU186 | smpA | CDS | F | 202263 | 202571 | small protein A |
| BU187 | ydhD | CDS | F | 203108 | 203434 | hypothetical protein |
| BU188 | rnt | CDS | R | 203578 | 204243 | ribonuclease T |
| BU189 | sodA | CDS | F | 204463 | 205074 | superoxide dismutase |
| BU190 | pth | CDS | F | 205262 | 205795 | peptidyl-tRNA hydrolase |
| BU191 | ychF | CDS | F | 205836 | 206924 | probable GTP-binding protein |
| BU192 | thrC | CDS | R | 207000 | 208289 | threonine synthase |
| BU193 | thrB | CDS | R | 208296 | 209225 | homoserine kinase |
| BU194 | thrA | CDS | R | 209246 | 211696 | aspartokinase I/homoserine dehydrogenase I |
| BU195 | hpt | CDS | F | 212355 | 212855 | hypoxanthine phosphoribosyltransferase |
| BU196 | panC | CDS | R | 212899 | 213756 | pantoate-beta-alanine ligase |
| BU197 | panB | CDS | R | 213771 | 214562 | 3-methyl-2-oxobutanoate hydroxymethyltransferase |
| BU198 | dksA | CDS | R | 214678 | 215133 | dnaK suppressor protein |
| BU199 | truA | CDS | F | 215390 | 216190 | pseudouridylate synthase I |
| BU200 | mrcB | CDS | F | 216262 | 218544 | penicillin-binding protein 1b |
| BU201 | secA | CDS | F | 218774 | 221401 | preprotein translocase secA subunit |
| BU202 | mutT | CDS | F | 221477 | 221851 | mutator mutT protein |
| BU203 | yacE | CDS | R | 221834 | 222487 | hypothetical protein |
| BU204 | guaC | CDS | F | 222543 | 223592 | GMP reductase |
| BU205 | aceE | CDS | F | 223819 | 226482 | pyruvate dehydrogenase e1 component |
| BU206 | aceF | CDS | F | 226513 | 227703 | dihydrolipoamide acetyltransferase |
| BU207 | lpdA | CDS | F | 227748 | 229169 | dihydrolipoamide dehydrogenase |
| BU208 | speD | CDS | R | 229342 | 230139 | S-adenosylmethionine decarboxylase proenzyme |
| Bu209 | speE | CDS | R | 230158 | 231018 | spermidine synthase |
| BU210 | pfs | CDS | R | 231294 | 231992 | 5-methylthioadenosine/S-adenosylhomocysteine nucleosidase |
| BU211 | yadR | CDS | R | 232056 | 232400 | hypothetical protein |
| BU212 | ftsZ | CDS | R | 232634 | 233788 | cell division protein ftsZ |
| Bu213 | ftsA | CDS | R | 233846 | 235102 | cell division protein ftsA |

TABLE 1-continued

| ID | gene name | type[a] | orientation | start (bp) | end (bp) | description |
|---|---|---|---|---|---|---|
| Bu214 | ddlB | PS | R | 235298 | 236220 | D-alanine-D-alanine ligase B (D-alanylalanine synthetase) |
| BU215 | murC | CDS | R | 236217 | 237671 | UDP-N-acetylmuramate-alanine ligase |
| BU216 | murG | CDS | R | 237714 | 238778 | UDP-N-acetylglucosamine-N-acetylmuramyl-(pentapeptide) pyrophosphoryl-undecaprenol N-acetylglucosamine transferase |
| BU217 | ftsW | CDS | R | 238775 | 239974 | cell division protein ftsW |
| BU218 | murD | CDS | R | 239971 | 241293 | UDP-N-acetylmuramoylalanine-D-glutamate ligase |
| BU219 | mraY | CDS | R | 241293 | 242366 | phospho-N-acetylmuramoyl-pentapeptide-transferase |
| BU220 | murF | CDS | R | 242360 | 243727 | UDP-N-acetylmuramoylalanyl-D-glutamyl-2,6-diaminopimelate-D-alanyl-D-alanyl ligase |
| BU221 | murE | CDS | R | 243724 | 245217 | UDP-N-acetylmuramoylalanyl-D-glutamate-2,6-diaminopimelate ligase |
| BU222 | ftsI | CDS | R | 245218 | 246957 | cell division protein ftsI |
| BU223 | ftsL | CDS | R | 247072 | 247275 | cell division protein ftsL |
| BU224 | yabC | CDS | R | 247278 | 248216 | hypothetical protein |
| BU225 | ilvH | CDS | R | 248338 | 248814 | acetolactate synthase small subunit |
| BU226 | ilvI | CDS | R | 248819 | 250534 | acetolactate synthase large subunit |
| BU227 | apbE | PS | R | 250805 | 251880 | thiamine biosynthesis lipoprotein ApbE precursor |
| BU228 | htrA | CDS | F | 252152 | 253588 | protease do precursor |
| BU229 | dapD | CDS | R | 253632 | 254456 | 2,3,4,5-tetrahydropyridine-2-carboxylate N-succinyltransferase |
| BU230 | map | CDS | R | 254517 | 255311 | methionine aminopeptidase |
| BU231 | rpsB | CDS | F | 255574 | 256308 | 30S ribosomal protein S2 |
| BU232 | tsf | CDS | F | 256385 | 257191 | elongation factor Ts |
| BU233 | pyrH | CDS | F | 257242 | 257970 | uridylate kinase |
| BU234 | frr | CDS | F | 258051 | 258608 | ribosome recycling factor |
| BU235 | dxr | CDS | F | 256691 | 259887 | 1-deoxy-D-xylulose 5-phosphate reductoisomerase |
| BU236 | uppS | CDS | F | 259980 | 260735 | undecaprenyl pyrophosphate synthetase |
| BU237 | yaeT | CDS | F | 260969 | 262822 | hypothetical protein |
| BU238 | dnaE | CDS | F | 262859 | 266344 | DNA polymerase III alpha chain |
| BU239 | proS | CDS | R | 266472 | 268190 | prolyl-tRNA synthetase |
| BU240 | flhB | CDS | F | 268530 | 269681 | flagellar biosynthetic protein flhB |
| BU241 | flhA | CDS | F | 269665 | 271764 | flagellar biosynthesis protein flhA |
| BU242 | argS | CDS | R | 271888 | 273612 | arginyl-tRNA synthetase |
| BU243 | rrs | rRNA | F | 274065 | 275524 | 16S rRNA |
| BU244 | tRNA-Ile | tRNA | F | 275637 | 275713 | tRNA-Ile (GAT) |
| BU245 | tRNA-Ala | tRNA | F | 275728 | 275800 | tRNA-Ala (TGC) |
| BU246 | gloB | CDS | R | 275795 | 276550 | probable hydroxyacylglutathione hydrolase |
| BU247 | rnhA | PS | R | 276591 | 277060 | ribonuclease hi (RNase hi) (ribonuclease H) (RNase H) |
| BU248 | dnaQ | CDS | F | 277113 | 277826 | DNA polymerase III epsilon chain |
| BU249 | tRNA-Asp | tRNA | F | 277895 | 277968 | tRNA-Asp (GTC) |
| BU250 | lpcA | CDS | F | 278052 | 278633 | phosphoheptose isomerase |
| BU251 | gpt | CDS | F | 278770 | 279216 | xanthine-guanine phosphoribosyltransferase |
| BU252 | grpE1 | CDS | F | 279317 | 279901 | heat shock protein grpE 1 |
| BU253 | yfjF | CDS | R | 279980 | 280279 | hypothetical protein |
| BU254 | smpB | CDS | F | 280373 | 280861 | small protein B |
| BU255 | yfhC | CDS | F | 280870 | 281355 | hypothetical protein yfhC |
| BU256 | acpS | CDS | R | 281356 | 281736 | holo-[acyl-carrier protein] synthase |
| BU257 | era | CDS | R | 281861 | 282712 | GTP-binding protein era |
| BU258 | rnc | CDS | R | 282709 | 283389 | ribonuclease III |
| BU259 | lepB | CDS | R | 283520 | 284464 | signal peptidase I |
| BU260 | lepA | CDS | R | 284480 | 286312 | GTP-binding protein lepA |
| BU261 | trmU | CDS | F | 286436 | 287614 | tRNA (5-methylaminomethyl-2-thiouridylate)-methyltransferase |
| BU262 | ycfC | CDS | F | 287650 | 288285 | hypothetical protein |
| BU263 | purB | CDS | F | 288324 | 289694 | adenylosuccinate lyase |
| BU264 | mltE | CDS | F | 289718 | 290383 | membrane-bound lytic murein transglycosylase E |
| BU265 | fabI | CDS | F | 290497 | 291279 | enoyl-[acyl-carrier-protein] reductase (NADH) |
| BU266 | rnb | CDS | F | 291466 | 293415 | exoribonuclease II |
| BU267 | ychE | CDS | F | 293524 | 294171 | hypothetical protein |
| BU268 | lipB | CDS | F | 294209 | 294844 | lipoate-protein ligase B |
| BU269 | lipA | CDS | F | 294963 | 295934 | lipoic acid synthetase |
| BU270 | pyrF | CDS | F | 296039 | 296749 | orotidine 5'-phosphate decarboxylase |
| BU271 | ribA | CDS | F | 296797 | 297381 | GTP cyclohydrolase II |
| BU272 | hns | CDS | R | 297485 | 297970 | DNA-binding protein H-ns |
| BU273 | cls | CDS | R | 298238 | 299698 | cardiolipin synthetase |
| BU274 | yciA | CDS | R | 300079 | 300486 | hypothetical protein |
| BU275 | yciB | CDS | R | 300523 | 301056 | hypothetical protein |
| BU276 | yciC | CDS | R | 301084 | 301827 | hypothetical protein |
| BU277 | trpA | CDS | R | 301932 | 302741 | tryptophan synthase alpha chain |
| BU278 | trpB | CDS | R | 302760 | 303926 | tryptophan synthase beta chain |
| BU279 | trpC | CDS | R | 303964 | 305325 | indole-3-glycerol phosphate synthase/N-(5'-phospho-ribosyl)anthranilate isomerase |
| BU280 | rpD | CDS | R | 305306 | 306334 | anthranilate phosphoribosyltransferase |
| BU281 | yedA | CDS | F | 306569 | 307492 | hypothetical protein |

TABLE 1-continued

| ID | gene name | type[a] | orientation | start (bp) | end (bp) | description |
|---|---|---|---|---|---|---|
| BU282 | yciL | CDS | F | 307521 | 308273 | hypothetical protein |
| BU283 | sohB | CDS | F | 308270 | 309358 | possible protease sohB |
| BU284 | topA | CDS | F | 309445 | 312030 | DNA topoisomerase I |
| BU285 | suhB | CDS | R | 312083 | 312883 | extragenic suppressor protein suhB |
| BU286 | yfgB | CDS | F | 313130 | 314221 | hypothetical protein |
| BU287 | gcpE | CDS | F | 314272 | 315378 | gcpE protein |
| BU288 | hisS | CDS | F | 315404 | 316675 | histidyl-tRNA synthetase |
| BU289 | glyA | CDS | F | 316735 | 317988 | serine hydroxymethyltransferase |
| BU290 | bioD | CDS | R | 318076 | 318750 | dethiobiotin synthetase |
| BU291 | bioB | CDS | F | 320225 | 321511 | adenosylmethionine-8-amino-7-oxononanoate aminotransferase |
| BU292 | bioA | CDS | F | 320225 | 321511 | adenosylmethiuonine-8-amino-7-oxononanoate aminotransferase |
| BU293 | ybhE | CDS | R | 321520 | 322524 | hypothetical protein |
| BU294 | mfd | CDS | R | 322648 | 325086 | transcription-repair coupling factor |
| BU295 | ycfU | CDS | F | 325561 | 326760 | hypothetical protein |
| BU296 | ycfV | CDS | F | 326753 | 327439 | hypothetical ABC transporter ATP-binding protein ycfv |
| BU297 | ycfW | PS | F | 327457 | 328694 | hypothetical ABC transporter membrane component ycfW |
| BU298 | gapA | CDS | F | 328764 | 329774 | glyceraldehyde 3-phosphate dehydrogenase A |
| BU299 | fldA | CDS | R | 330105 | 330620 | flavodoxin 1 |
| BU300 | phrB | CDS | F | 330827 | 332278 | deoxyribodipyrimidine photolyase |
| BU301 | ybgI | CDS | F | 332275 | 33018 | hypothetical protein |
| BU302 | sucA | CDS | F | 333143 | 335872 | 2-oxoglutarate dehydrogenasxe e1 component |
| BU303 | sucB | CDS | F | 335888 | 337150 | dihydrolipoamide succinyltransferase component (E2) of 2-oxoglutarate dehydrogenase complex |
| BU304 | gpmA | CDS | F | 337248 | 337943 | phosphoglycerate mutase |
| BU305 | pfkA | CDS | F | 338127 | 339089 | 6-phosphofructokinase isozyme I |
| BU306 | glfF | CDS | F | 339155 | 339946 | glycerol uptake facilitator protein |
| BU307 | tpiA | CDS | R | 339955 | 340722 | triosephosphate isomerase |
| BU308 | himD | CDS | R | 340821 | 341105 | integration host factor beta-subunit |
| BU309 | rpsA | CDS | R | 341201 | 342877 | 30S ribosomal protein S1 |
| BU310 | cmk | PS | R | 343005 | 343660 | cytidylate kinase |
| BU311 | aroA | CDS | R | 343716 | 344999 | 3-phosphoshikimate 1-carboxyvinyltransferase |
| BU312 | serC | CDS | R | 345066 | 346151 | phosphoserine aminotransferase |
| BU313 | serS | CDS | R | 346190 | 347473 | seryl-tRNA synthetase |
| BU314 | trxB | CDS | F | 347821 | 348780 | thioredoxin reductase |
| BU315 | infA | CDS | F | 348887 | 349105 | translation initiation factor IF-1 |
| BU316 | aspS | CDS | F | 349274 | 351034 | aspartyl-tRNA synthetase |
| BU317 | znuB | CDS | R | 351045 | 351833 | high-affinity zinc uptake system membrane protein ZnuB |
| BU318 | znuC | CDS | R | 351891 | 352607 | high-affinity zinc uptake system ATP-binding protein ZnuC |
| BU319 | pykA | CDS | R | 353925 | 355367 | pyruvate kinase |
| BU320 | zwf | CDS | F | 355650 | 357125 | glucose-6-phosphate 1-dehydrogenase |
| BU321 | htpX | CDS | F | 357310 | 358188 | heat shock protein htpX |
| BU322 | cspC | CDS | F | 358537 | 358746 | cold shock-like protein cspC |
| BU323 | yoaE | CDS | F | 359049 | 360614 | hypothetical protein |
| BU324 | yeaZ | CDS | F | 360644 | 361309 | hypothetical protein |
| BU325 | minE | CDS | R | 361455 | 361706 | cell division topological specificity factor |
| BU326 | minD | CDS | R | 361710 | 362522 | septum site-determining protein minD |
| BU327 | minC | DCS | R | 362549 | 363262 | cell division inhibitor minC |
| BU328 | yjjT | CDS | F | 363663 | 364505 | hypothetical protein |
| BU329 | tRNA-Leu | tRNA | R | 364524 | 364607 | tRNA-Leu (TAA) |
| BU330 | tRNA-Cys | tRNA | R | 364619 | 364692 | tRNA-Pseudo (GCA) |
| BU331 | tRNA-Ser | tRNA | F | 364863 | 364947 | tRNA-Ser (TGA) |
| BU332 | ompA | CDS | R | 365056 | 366105 | outer membrane protein A precursor |
| BU333 | mviN | CDS | R | 366242 | 367777 | virulence factor mviN homolog |
| BU334 | pyrC | CDS | F | 368052 | 369104 | dihydroorotase |
| BU335 | flgN | CDS | R | 369124 | 369531 | flagella synthesis protein flgN |
| BU336 | flgA | CDS | R | 369604 | 370284 | flagella basal body P-ring formation protein flgA precursor |
| BU337 | flgB | CDS | F | 370621 | 370968 | flagellar basal-body rod protein flgB |
| BU338 | flgC | CDS | F | 370977 | 371387 | flagellar basal-body rod protein flgC |
| BU339 | flgD | CDS | F | 371399 | 372109 | basal-body rod modification protein flgD |
| BU340 | flgE | CDS | F | 372159 | 373376 | flagellar hook protein flgE |
| BU341 | flgF | CDS | F | 373427 | 374161 | flagellar basal-body rod protein flgF |
| BU342 | flgG | CDS | F | 374179 | 374961 | flagellar basal-body rod protein flgG |
| BU343 | flgH | CDS | F | 375045 | 375761 | flagellar L-ring protein precursor |
| BU344 | flgI | CDS | F | 375942 | 377099 | flagellar P-ring protein precursor |
| BU345 | flgJ | CDS | F | 377099 | 377398 | flagellar protein flgJ |
| BU346 | flgK | CDS | F | 377500 | 379131 | flagellar hook-associated protein 1 |
| BU347 | rne | CDS | R | 379296 | 382004 | ribonuclease E |
| BU348 | rluC | CDS | F | 382339 | 383283 | ribosomal large subunit pseudouridine synthase C |
| BU349 | rpmF | CDS | F | 383329 | 383493 | 50S ribosomal protein L32 |
| BU350 | fabD | PS | F | 383914 | 384872 | malonyl CoA-acyl carrier protein transacylase (MCT) |
| BU351 | fabG | CDS | F | 384859 | 385593 | 3-oxoacyl-[acyl-carrier protein] reductase |

TABLE 1-continued

| ID | gene name | type[a] | orientation | start (bp) | end (bp) | description |
|---|---|---|---|---|---|---|
| BU352 | acpP | CDS | F | 385670 | 385912 | acyl carrier protein |
| BU353 | tmk | CDS | F | 385983 | 386621 | thymidylate kinase |
| BU354 | holB | CDS | F | 386618 | 38759b | DNA polymerase III delta' subunit |
| BU355 | ycfH | CDS | F | 387632 | 388426 | hypothetical protein |
| BU356 | ptsG | CDS | F | 388571 | 389956 | pts system glucose-specific IIBC component |
| BU357 | vcfF | CDS | F | 389976 | 390320 | hypothetical protein |
| BU358 | ycfM | CDS | F | 390397 | 390906 | hypothetical protein |
| BU359 | ompF | CDS | R | 391155 | 392303 | ompF-like porin |
| BU360 | asnS | CDS | R | 392443 | 393843 | asparaginyl-tRNA synthetase |
| BU361 | pncB | CDS | R | 393991 | 395190 | nicotinate phosphoribosyltransferase |
| BU362 | pyrD | CDS | F | 395612 | 396475 | dihydroorotate dehydrogenase |
| BU363 | ycbY | CDS | F | 396651 | 398756 | hypothetical protein |
| BU364 | uup | CDS | F | 398776 | 400566 | ABC transporter ATP-binding protein uup |
| BU365 | yceA | CDS | R | 400570 | 401544 | hypothetical protein |
| BU366 | valS | CDS | R | 401601 | 404468 | valyl-tRNA synthetase |
| BU367 | pepA | CDS | R | 404545 | 406044 | aminopeptidase A/I |
| BU368 | argF | CDS | F | 406304 | 407320 | ornithine carbamoyltransferase chain F |
| BU369 | pyrB | CDS | F | 407439 | 408371 | aspartate carbamoyltransferase catalytic chain |
| BU370 | pyrI | CDS | F | 408379 | 408843 | aspartate carbamoyltransferase regulatory chain |
| BU371 | yhaR | CDS | F | 408889 | 409275 | hypothetical protein |
| BU372 | deaD | CDS | R | 409362 | 411167 | ATP-dependent RNA helicase deaD |
| BU373 | pnp | CDS | R | 411548 | 413671 | polyribonucleotide nucleotidyltransferase |
| BU374 | rpsO | CDS | R | 413873 | 414142 | 30S ribosomal protein S15 |
| BU375 | truB | CDS | R | 414247 | 415185 | tRNA pseudouridine 55 synthase |
| BU376 | rbfA | CDS | R | 415223 | 415585 | ribosome-binding factor A |
| BU377 | infB | CDS | R | 415631 | 418225 | translation initiation factor IF-2 |
| BU378 | nusA | CDS | R | 418243 | 419733 | N utilization substance protein A |
| BU379 | tRNA-Leu | tRNA | R | 420072 | 420157 | tRNA-Leu (GAG) |
| BU380 | secG | CDS | R | 420206 | 420535 | protein-export membrane protein secG |
| BU381 | mrsA | CDS | R | 420797 | 422131 | mrsA protein |
| BU382 | hflB | CDS | R | 422351 | 424141 | cell division protein ftsh |
| BU383 | ftsJ | CDS | R | 424252 | 424872 | cell division protein ftsJ |
| BU384 | greA | CDS | R | 424946 | 425425 | transcription elongation factor greA |
| BU385 | yrbA | CDS | F | 425949 | 426191 | hypothetical protein |
| BU386 | murA | CDS | F | 426253 | 427503 | UDP-N-acetylglucosamine 1-carboxyvinyltransferase |
| BU387 | rplU | CDS | F | 427642 | 427968 | 50S ribosomal protein L21 |
| BU388 | rpmA | CDS | F | 427973 | 428227 | 50S ribosomal protein L27 |
| BU389 | yhbZ | CDS | F | 428379 | 429383 | hypothetical 43.3 kD GTP-binding protein in dacB-rpmA intergenic region (F390) |
| BU390 | rpsI | CDS | R | 429451 | 429843 | 30S ribosomal protein S9 |
| BU391 | rplM | CDS | R | 429864 | 430292 | 50S ribosomal protein L13 |
| BU392 | pheA | CDS | F | 430544 | 431701 | chorismate mutase/prephenate dehydratase |
| BU393 | ffh | CDS | F | 431883 | 433238 | signal recognition particle protein |
| BU394 | rpsP | CDS | F | 433347 | 433586 | 30S ribosomal protein S16 |
| BU395 | rimM | CDS | F | 433588 | 434118 | 16s rRNA processing protein rimm |
| BU396 | trmD | CDS | F | 434133 | 434846 | tRNA (guanine-n1)-methyltransferase |
| BU397 | rplS | CDS | F | 434945 | 435292 | 50S ribosomal protein L19 |
| BU398 | t/dD | CDS | R | 435376 | 436827 | tldD protein |
| BU399 | aroD | CDS | F | 436965 | 437437 | type II 3-dehydroquinase |
| BU400 | fis | CDS | R | 437630 | 437926 | factor-for-inversion stimulation protein |
| BU401 | rluD | CDS | R | 438095 | 439033 | ribosomal large subunit pseudouridine synthase D |
| BU402 | yfiO | CDS | F | 439198 | 439938 | hypothetical protein |
| BU403 | alaS | CDS | F | 440103 | 442739 | alanyl-tRNA synthetase |
| BU404 | csrA | CDS | F | 442934 | 443107 | carbon storage regulator |
| BU405 | tRNA-Ser | tRNA | F | 443263 | 443354 | tRNA-Ser (GCT) |
| BU406 | tRNA-Arg | tRNA | F | 443372 | 443445 | tRNA-Arg (ACG) |
| BU407 | gshA | CDS | F | 443565 | 445121 | glutamate-cysteine ligase |
| BU408 | metK | CDS | R | 445268 | 446404 | S-adenosylmethionine synthetase |
| BU409 | endA | CDS | F | 446639 | 447391 | endonuclease I |
| BU410 | yggJ | CDS | F | 447363 | 448124 | hypothetical protein |
| BU411 | rp/A | CDS | R | 448198 | 448869 | ribose 5-phosphate isomerase A |
| BU412 | tRNA-Gln | tRNA | R | 449053 | 449127 | tRNA-Gln (TTG) |
| BU413 | tRNA-Leu | tRNA | R | 449220 | 449301 | tRNA-Leu (TAG) |
| BU414 | tRNA-Met | tRNA | R | 449313 | 449389 | tRNA-Met (CAT) |
| BU415 | glnS | CDS | F | 449495 | 451210 | glutaminyl-tRNA synthetase |
| BU416 | pyrG | CDS | F | 451384 | 453021 | CTP synthase |
| BU417 | eno | CDS | F | 453051 | 454355 | enolase |
| BU418 | nlpD | CDS | R | 454513 | 455517 | lipoprotein nipD precursor |
| BU419 | ygbB | CDS | R | 455608 | 456093 | hypothetical protein |
| BU420 | ygbP | CDS | R | 456109 | 456822 | hypothetical protein |
| BU421 | ygbQ | CDS | R | 456905 | 457120 | hypothetical protein |
| BU422 | cysC | CDS | R | 457178 | 457798 | adenylylsulfate kinase |
| BU423 | cysN | CDS | R | 457799 | 459220 | sulfate adenylate transferase subunit 1 |
| BU424 | cysD | CDS | R | 459239 | 460147 | sulfate adenylate transferase subunit 2 |
| BU425 | cysG | CDS | R | 460157 | 461578 | siroheme synthase/precorrin-2 oxidase/ferrochelatase |
| BU426 | cysH | CDS | R | 461917 | 462651 | phosphoadenosine phosphosulfate reductase |

TABLE 1-continued

| ID | gene name | type[a] | orientation | start (bp) | end (bp) | description |
|---|---|---|---|---|---|---|
| BU427 | cysI | CDS | R | 462667 | 464376 | sulfite reductase (NADPH) hemoprotein beta-component |
| BU428 | cysJ | CDS | R | 464376 | 466181 | sulfite reductase (NADPH) flavoprotein alpha-component |
| BU429 | mutS | CDS | R | 466372 | 468780 | DNA mismatch repair protein mutS |
| BU430 | dsbA | CDS | F | 468937 | 469575 | thiol:disulfide interchange protein dsbA precursor |
| BU431 | poiA | CDS | F | 469696 | 470556 | DNA polymerase I |
| BU432 | yihA | CDS | R | 470619 | 471236 | hypothetical GTP-binding protein |
| BU433 | typA | CDS | F | 471487 | 473310 | GTP-binding protein TypA/BipA |
| BU434 | gmk | CDS | R | 473433 | 474056 | guanylate kinase |
| BU435 | ygfZ | CDS | R | 474156 | 475115 | hypothetical protein |
| BU436 | prfB | CDS | F | 475334 | 476383 | peptide chain release factor 2 |
| BU437 | lysS | CDS | F | 476393 | 477913 | lysyl-tRNA synthetase |
| BU438 | lysA | CDS | F | 477979 | 479226 | diaminopimelate decarboxylase |
| BU439 | lgt | CDS | F | 479292 | 480137 | prolipoprotein diacylglyceryl transferase |
| BU440 | thyA | CDS | F | 480151 | 480945 | thymidylate synthase |
| BU441 | yleA | CDS | F | 481012 | 482331 | hypothetical protein |
| BU442 | ybeY | CDS | F | 482486 | 482821 | hypothetical protein |
| BU443 | ybeX | CDS | F | 482902 | 483777 | hypothetical protein |
| BU444 | leuS | CDS | F | 483881 | 486460 | leucyl-tRNA synthetase |
| BU445 | holA | CDS | F | 486500 | 487495 | DNA polymerase III delta subunit |
| BU446 | ybeN | CDS | F | 487518 | 488162 | hypothetical protein |
| BU447 | yhhP | CDS | F | 488223 | 488453 | hypothetical protein |
| BU448 | asd | CDS | R | 488600 | 489715 | aspartate-semialdehyde dehydrogenase |
| BU449 | yhgN | CDS | F | 490053 | 490601 | hypothetical protein |
| BU450 | pgk | CDS | F | 490715 | 491887 | phosphoglycerate kinase |
| BU451 | fba | CDS | F | 491903 | 492979 | fructose-bisphosphate aldolase |
| BU452 | yggB | CDS | F | 493043 | 493960 | hypothetical protein |
| BU453 | recC | CDS | F | 494019 | 497231 | exodeoxyribonuclease V 125 kD polypeptide |
| BU454 | recB | CDS | F | 497248 | 500772 | exodeoxyribonuclease V 135 kD polypeptide |
| BU455 | recD | CDS | F | 500778 | 502586 | exodeoxyribonuclease V 67 kD polypeptide |
| BU456 | argA | CDS | R | 502625 | 503953 | amino-acid acetyltransferase |
| BU457 | tRNA-Met | tRNA | R | 504133 | 504209 | tRNA-Met (CAT) |
| BU458 | mltA | CDS | F | 504321 | 505400 | membrane-bound lytic murein transglycosylase A precursor |
| BU459 | ribH | CDS | F | 505439 | 505921 | 6,7-dimethyl-8-ribityllumazine synthase |
| BU460 | thiL | CDS | F | 505951 | 506922 | thiamin-monophosphate kinase |
| BU461 | ribD1 | CDS | F | 506978 | 507403 | riboflavin deaminase |
| BU462 | ribD2 | CDS | F | 507446 | 508069 | riboflavin reductase |
| BU463 | nusB | CDS | F | 508106 | 508537 | N utilization substance protein B |
| BU464 | dxs | CDS | R | 508592 | 510418 | dxs protein |
| BU465 | ispA | CDS | R | 510476 | 511324 | geranyltranstransferase |
| BU466 | yajR | CDS | R | 511376 | 512548 | hypothetical protein |
| BU467 | yccK | CDS | F | 512622 | 512966 | hypothetical protein |
| BU468 | cyoE | CDS | R | 512987 | 513844 | protohaeme IX farnesyltransferase |
| BU469 | cyoD | CDS | R | 513872 | 514189 | cytochrome o ubiquinol oxidase subunit IV |
| BU470 | cyoC | CDS | R | 514189 | 514806 | cytochrome o ubiquinol oxidase subunit III |
| BU471 | cyoB | CDS | R | 514803 | 516791 | cytochrome o ubiquinol oxidase subunit I |
| BU472 | cyoA | CDS | R | 516796 | 517686 | cytochrome o ubiquinol oxidase subunit II |
| BU473 | bolA | CDS | F | 517985 | 518299 | bolA protein |
| BU474 | tig | CDS | F | 518435 | 519763 | trigger factor |
| BU475 | clpP | CDS | F | 519898 | 520524 | ATP-dependent clp protease proteolytic subunit |
| BU476 | clpX | CDS | F | 520623 | 521912 | ATP-dependent clp protease ATP-binding subunit clpX |
| BU477 | lon | CDS | F | 522104 | 524437 | ATP-dependent protease La |
| BU478 | ppiD | CDS | F | 524579 | 526450 | peptidyl-prolyl cis-trans isomerase D |
| BU479 | mdl | CDS | F | 527423 | 529192 | multidrug resistance-like ATP-binding protein mdl |
| BU480 | mdlB | CDS | F | 529164 | 530936 | mdlB |
| BU481 | dnaX | CDS | F | 531231 | 532316 | DNA polymerase III subunits gamma and tau |
| BU482 | ybaB | CDS | F | 532636 | 532965 | hypothetical protein |
| BU483 | htpG | CDS | F | 533111 | 534985 | heat shock protein htpG |
| BU484 | adk | CDS | F | 535058 | 535705 | adenylate kinase |
| BU485 | tRNA-Arg | tRNA | R | 535708 | 535781 | tRNA-Arg (TCT) |
| BU486 | folD | CDS | F | 535936 | 536793 | methylenetetrahydrofolate dehydrogenase/methenyltetrahydrofolate cyclohydrolase |
| BU487 | cysS | CDS | R | 536790 | 538184 | cysteinyl-tRNA synthetase |
| BU488 | ybeD | CDS | F | 538445 | 538708 | hypothetical protein |
| BU489 | cspE | CDS | R | 538815 | 539024 | cold shock-like protein cspE |
| BU490 | rrf | rRNA | R | 539312 | 539426 | 5S rRNA |
| BU491 | rrl | rRNA | R | 539539 | 542451 | 23S rRNA |
| BU492 | tRNA-Glu | tRNA | R | 542613 | 542685 | tRNA-Glu (TTC) |
| BU493 | aroE | 00$ | R | 542838 | 543659 | shikimate 5-dehydrogenase |
| BU494 | yrdC | CDS | R | 543652 | 544179 | hypothetical protein |
| BU495 | smg | CDS | R | 544277 | 544750 | smg protein |
| BU496 | def | CDS | F | 544994 | 545515 | polypeptide deformylase |
| BU497 | fmt | CDS | F | 545523 | 546467 | methionyl-tRNA formyltransferase |
| BU498 | rplQ | CDS | R | 546594 | 546986 | 50S ribosomal protein L17 |
| BU499 | rpoA | CDS | R | 547031 | 548020 | DNA-directed RNA polymerase alpha chain |

TABLE 1-continued

| ID | gene name | type[a] | orientation | start (bp) | end (bp) | description |
|---|---|---|---|---|---|---|
| BU500 | rpsD | CDS | R | 548049 | 548669 | 30S ribosomal protein S4 |
| BU501 | rpsK | CDS | R | 548695 | 549090 | 30S ribosomal protein S11 |
| BU502 | rpsM | CDS | R | 549108 | 549464 | 30S ribosomal protein S13 |
| BU503 | rpmJ | CDS | R | 549558 | 549674 | 50S ribosomal protein L36 |
| BU504 | secY | CDS | R | 549700 | 551013 | preprotein translocase secY subunit |
| BU505 | rplO | CDS | R | 551024 | 551458 | 50S ribosomal protein L15 |
| BU506 | rpmD | CDS | R | 551463 | 551642 | 50S ribosomal protein L30 |
| BU507 | rpsE | CDS | R | 551652 | 552155 | 30S ribosomal protein S5 |
| BU508 | rplR | CDS | R | 552171 | 552539 | 50S ribosomal protein L18 |
| BU509 | rplF | CDS | R | 552541 | 553113 | 50S ribosomal protein L6 |
| BU510 | rpsH | CDS | R | 553088 | 553480 | 30S ribosomal protein S8 |
| BU511 | rpsN | CDS | R | 553509 | 553814 | 30S ribosomal protein S14 |
| BU512 | rplE | CDS | R | 553832 | 554371 | 50S ribosomal protein L5 |
| BU513 | rplX | CDS | R | 554386 | 554700 | 50S ribosomal protein L24 |
| BU514 | rplN | CDS | R | 554726 | 555094 | 50S ribosomal protein L14 |
| BU515 | rpsQ | CDS | R | 555209 | 555460 | 30S ribosomal protein S17 |
| BU516 | rpmC | CDS | R | 555460 | 555657 | 50S ribosomal protein L29 |
| BU517 | rplP | CDS | R | 555657 | 556067 | 50S ribosomal protein L16 |
| BU518 | rpsC | CDS | R | 556088 | 556789 | 30S ribosomal protein S3 |
| BU519 | rplV | CDS | R | 556808 | 557140 | 50S ribosomal protein L22 |
| BU520 | rpsS | CDS | R | 557176 | 557454 | 30S ribosomal protein S19 |
| BU521 | rplB | CDS | R | 557474 | 558295 | 50S ribosomal protein L2 |
| BU522 | rplW | CDS | R | 558310 | 558612 | 50S ribosomal protein L23 |
| BU523 | rplD | CDS | R | 558609 | 559214 | 50S ribosomal protein L4 |
| BU524 | rplC | CDS | R | 559232 | 559861 | 50S ribosomal protein L3 |
| BU525 | rpsJ | CDS | R | 559892 | 560203 | 30S ribosomal protein S10 |
| BU526 | tufB | CDS | R | 560535 | 561806 | elongation factor EF-Tu |
| BU527 | fusA | CDS | R | 561787 | 563895 | elongation factor G |
| BU528 | rpsG | CDS | R | 564010 | 564480 | 30S ribosomal protein S7 |
| BU529 | rpsL | CDS | R | 564522 | 564896 | 30S ribosomal protein S12 |
| BU530 | yheL | CDS | R | 565030 | 565302 | hypothetical protein |
| BU531 | yheM | CDS | R | 565329 | 565688 | hypothetical protein |
| BU532 | yheN | CDS | R | 56S707 | 566093 | hypothetical protein |
| BU533 | fkpA | CDS | R | 566176 | 566901 | fkbp-type peptidyl-prolyl cis-trans isomerase fkpA precursor |
| BU534 | argD | CDS | R | 567364 | 568590 | acetylornithine aminotransferase |
| BU535 | yhfC | CDS | F | 568906 | 570072 | hypothetical protein |
| BU536 | trpS | CDS | R | 670134 | 571141 | tryptophanyl-tRNA synthetase |
| BU537 | rpe | CDS | R | 571164 | 571850 | ribulose-phosphate 3-epimerase |
| BU538 | aroB | CDS | R | 572734 | 573825 | 3-dehydroquinate synthase |
| BU539 | aroK | CDS | R | 573843 | 574364 | shikimate kinase I |
| BU540 | tRNA-Ser | tRNA | F | 574863 | 574947 | tRNA-Ser (GGA) |
| BU541 | deoD | CDS | R | 574967 | 575671 | purine nucleoside phosphorylase |
| BU542 | deoB | CDS | R | 575715 | 576938 | phosphopentomutase |
| BU543 | prfC | CDS | R | 576996 | 578576 | peptide chain release factor 3 |
| BU544 | yhgI | CDS | R | 579687 | 580265 | hypothetical protein |
| BU545 | ssb | CDS | R | 580878 | 581393 | single-strand binding protein |
| BU546 | dnaB | CDS | F | 582081 | 583460 | replicative DNA helicase |
| BU547 | gshB | CDS | F | 583707 | 584669 | glutathione synthetase |
| BU548 | yqgF | CDS | F | 584680 | 585087 | hypothetical protein |
| BU549 | yggS | CDS | F | 585205 | 585807 | hypothetical protein |
| BU550 | yggW | CDS | F | 585860 | 586980 | hypothetical protein |
| BU551 | yggH | CDS | R | 586987 | 587706 | hypothetical protein |
| BU552 | mutY | CDS | F | 587804 | 588856 | A/G-specific adenine glycosylase |
| BU553 | yggX | CDS | F | 588828 | 589109 | hypothetical protein |
| BU554 | muri | CDS | F | 589203 | 589991 | glutamate racemase |
| BU555 | sbcB | CDS | R | 590182 | 591423 | exodeoxyribonuclease I |
| BU556 | yeeX | CDS | F | 591503 | 591811 | hypothetical protein |
| BU557 | tRNA-Asn | tRNA | R | 591818 | 591890 | tRNA-Asn (GTT) |
| BU558 | tRNA-Met | tRNA | F | 592025 | 592097 | tRNA-Met (CAT) |
| BU559 | pyrE | CDS | F | 592193 | 592834 | orotate phosphoribosyltransferase |
| BU560 | dut | CDS | R | 592846 | 593310 | deoxyuridine 5'-triphosphate nucleotidohydrolase |
| BU561 | cysQ | CDS | R | 593354 | 594151 | cysQ protein |
| BU562 | rplI | CDS | R | 594138 | 594590 | 50S ribosomal protein L9 |
| BU563 | rpsR | CDS | R | 594639 | 594866 | 30S ribosomal protein S18 |
| BU564 | rpsF | CDS | R | 594992 | 595333 | 30S ribosomal protein S6 |
| BU565 | vacB | CDS | R | 595499 | 597736 | vacB protein |
| BU566 | purA | CDS | R | 597824 | 599125 | adenylosuccinate synthetase |
| BU567 | hflC | CDS | R | 599175 | 600107 | hflC protein |
| BU568 | hflK | CDS | R | 600110 | 601330 | hflK protein |
| BU569 | miaA | CDS | R | 601487 | 602395 | tRNA delta(2)-isopentenylpyrophosphate transferase |
| BU570 | mutL | CDS | R | 602433 | 604187 | DNA mismatch repair protein mutL |
| BU571 | mtlD | CDS | R | 604287 | 605444 | mannitol-1-phosphate 5-dehydrogenase |
| BU572 | mtlA | CDS | R | 605486 | 607384 | pts system mannitol-specific II ABC component |
| BU573 | pgi | CDS | R | 607559 | 609208 | glucose-6-phosphate isomerase |
| BU574 | orn | CDS | F | 609522 | 610076 | oligoribonuclease |
| BU575 | tRNA-Gly | tRNA | F | 610162 | 610237 | tRNA-Gly (GCC) |

TABLE 1-continued

| ID | gene name | type[a] | orientation | start (bp) | end (bp) | description |
|---|---|---|---|---|---|---|
| BU576 | amiB | CDS | F | 610528 | 611241 | N-acetylmuramoyl-L-alanine amidase precursor |
| BU577 | rpmE | CDS | R | 611349 | 611567 | 50S ribosomal protein L31 |
| BU578 | hslV | CDS | F | 612173 | 612685 | heat shock protein hslV |
| BU579 | hslU | CDS | F | 612698 | 614029 | heat shock protein hslU |
| BU580 | ibpA | CDS | F | 614236 | 614709 | 16 kD heat shock protein A |
| BU581 | fpr | CDS | F | 614786 | 615544 | ferredoxin-NADP reductase |
| BU582 | yjeA | CDS | R | 615562 | 616536 | hypothetical lysyl-tRNA synthetase homolog |
| BU583 | kdtB | CDS | F | 616608 | 617105 | lipopolysaccharide core biosynthesis protein kdtB |
| BU584 | yba3 | CDS | R | 617192 | 618295 | hypothetical protein |
| BU585 | yba4 | CDS | R | 618288 | 618626 | hypothetical protein |
| BU586 | yhiQ | CDS | F | 618781 | 619521 | hypothetical protein |
| BU587 | pitA | CDS | R | 619604 | 621076 | low-affinity inorganic phosphate transporter |
| BU588 | ynfM | CDS | R | 621227 | 622459 | hypothetical protein |
| BU589 | dapF | CDS | R | 622493 | 623410 | diaminopimelate epimerase |
| BU590 | cyaY | CDS | F | 623535 | 623885 | cyaY protein |
| BU591 | hemC | CDS | F | 624014 | 624958 | porphobilinogen deaminase |
| BU592 | hemD | PS | F | 624955 | 625712 | uroprophyrinogen-III synthase |
| BU593 | tRNA-Pro | tRNA | R | 625716 | 625792 | tRNA-Pro (TGG) |
| BU594 | tRNA-His | tRNA | R | 625829 | 625904 | tRNA-His (GTG) |
| BU595 | rho | CDS | R | 625934 | 626007 | tRNA-Arg (CCG) |
| BU596 | rho | CDS | R | 626196 | 627455 | transcription termination factor rho |
| BU597 | trxA | CDS | R | 627585 | 627911 | thioredoxin |
| BU598 | rep | CDS | R | 628113 | 630050 | ATP-dependent DNA helicase Rep |
| BU599 | ilvC | CDS | R | 630120 | 631592 | ketol-acid reductoisomerase |
| BU600 | ilvD | CDS | R | 631640 | 633493 | dihydroxy-acid dehydratase |
| BU601 | tRNA-Trp | tRNA | R | 633734 | 633807 | tRNA-Trp (CCA) |
| BU602 | yfhO | CDS | F | 633980 | 635194 | hypothetical protein |
| BU603 | iscU | CDS | F | 635225 | 635608 | hypothetical protein iscU |
| BU604 | hscB | CDS | F | 635703 | 636227 | chaperone protein hscB |
| BU605 | hscA | CDS | F | 636239 | 638074 | heat shock protein hscA |
| BU606 | fdx | CDS | F | 638074 | 638409 | ferredoxin 2fe-2s |
| BU607 | yfgK | CDS | R | 638406 | 639767 | hypothetical GTP-binding protein |
| BU608 | yfgM | CDS | R | 639860 | 640441 | hypothetical protein |

Next, each nucleotide sequence or its complementary sequence of the genes located between start points to end points of Table 1 is determined. Once the sequence has been determined, each of the genes can be obtained by chemical synthesis, by PCR using a nucleotide sequence at 5' or 3' end of the gene as a primer and using the whole or a part of genomic DNA (SEQ ID NO:1) as a template, or by hybridization using a nucleotide sequence of the gene described in Table 1 or DNA fragment having its complementary sequence thereof as a probe.

The genes of the present invention also include a gene hybridizing to the above-mentioned DNA under stringent conditions and encoding a protein having the same function as that of a product (a substance encoded by a sequence from "Start point" to "End point" in Table 1) expressed by the DNA.

The term "stringent conditions" means conditions by which specific hybrids are produced and non-specific hybrids are not produced. That is, DNAs that share high homology (60% or more homology, preferably 80% or more homology) hybridize to each other in such conditions. More specifically, sodium concentration ranges from 150 to 900 mM, preferably 600 to 900 mM, and temperature ranges from 60 to 68° C., preferably 65° C.

In addition to the above-described genomic DNA, plasmids can also be isolated from Buchnera sp. in this invention.

Plasmids of this invention can be prepared in the same manner as for genomic DNA. Nucleotide sequences of the plasmids of this invention are also determined simultaneously with the genomic chromosome by the above-mentioned shotgun sequencing.

Two types of the plasmids, pLeu and pTrp, are obtained as described above, each containing a self-replication sequence derived from Buchnera sp. The plasmids have the following sequences and possess features as shown in Table 2. Table 2 shows 11 genes contained in nucleotide sequences of the plasmids represented by SEQ ID NOS: 2 and 3.
pLeu (leucine plasmid): SEQ ID NO:2
pTrp (tryptophan plasmid): SEQ ID NO:3

TABLE 2

| ID | Gene name | Type | Orientation | Start point (bp) | End point (bp) | Description |
|---|---|---|---|---|---|---|
| pLeu plasmid | | | | | | |
| BUpL01 | repA1 | CDS | R | 346 | 1197 | putative replication-associated protein RepA1 |
| BUpL02 | yqhA | CDS | F | 1514 | 2017 | putative membrane-associated protein |
| BUpL03 | repA2 | CDS | F | 2357 | 2893 | putative replication-associated protein RepA2 |
| BUpL04 | leuA | CDS | F | 3032 | 4591 | 2-isopropylmalate synthase |
| BUpL05 | leuB | CDS | F | 4652 | 5743 | 3-isopropylmalate dehydrogenase |
| BUpL06 | leuC | CDS | F | 5733 | 7160 | 3-isopropylmalate dehydratase |
| BUpL07 | leuD | CDS | F | 7163 | 7786 | 3-isopropylmalate dehydratase small subunit |
| pTrp plasmid | | | | | | |
| BUpT01 | trpE | CDS | F | 1 | 1566 | anthranilate synthase large subunit |
| BUpT02 | trpG | CDS | F | 1569 | 2171 | anthranilate synthase small subunit |

TABLE 2-continued

| ID | Gene name | Type | Orientation | Start point (bp) | End point (bp) | Description |
|---|---|---|---|---|---|---|
| BUpT03 | trpE2 | PS | F | 3629 | 5122 | anthranilate synthase large subunit |
| BUpT04 | trpG2 | CDS | F | 5199 | 5801 | anthranilate synthase small subunit |

In Table 2, each column of "Orientation," "Type," "Start point," and "End point" represent the same as described in Table 1.

The plasmids of the present invention also include those containing DNA, capable of hybridizing to DNA comprising a nucleotide sequence of SEQ ID NO: 2 or 3 under stringent conditions, and self-replicating, in addition to those containing DNA comprising a nucleotide sequence of SEQ ID NO:2 or 3. The term "stringent conditions" can be defined as described above.

2. Construction of a recombinant vector and a transformant

Recombinant vectors of this invention can be obtained by ligating the above gene to an appropriate vector. A transformant can be obtained by introducing the recombinant vector of this invention into a host so that a gene of interest can be expressed.

Examples of vectors include phages or plasmids, which can autonomously replicate in host microorganisms. Examples of plasmid DNA include plasmids derived from *Escherichia coli* (for example, pBR322, pBR325, pUC118, pUC119, pUC18, and pUC19), plasmids derived from *Bacillus subtilis* (for example, pUB110, and pTP5), plasmids derived from yeast (for example, YEp13, YEp24, and YCp50). Examples of phage DNA include λ phage (Charon4A, Charon21A, EMBL3, EMBL4, λgt10, λgt11, and λZAP). Further, examples of vectors also include animal viruses, such as retro virus and vaccinia virus, and insect viruses, such as baculo virus.

To insert the gene of this invention into a vector, for example, purified DNA is cleaved with an appropriate restriction enzyme and inserted to a restriction enzyme site or multicloning site of an appropriate vector DNA so as to ligate to the vector.

The gene of this invention must be incorporated into a vector in order to exhibit its function. A promoter and the gene of this invention can be ligated to the vector of this invention. If necessary, a cis element, such as an enhancer, a splicing signal, a poly A addition signal, a selection marker, a ribosome binding sequence (SD sequence) can also be integrated to the vector. Examples of selection markers include dihydrofolic acid reducing enzyme gene, ampicillin-resistant gene, neomycin-resistant gene. In addition to vectors capable of replicating autonomously in two or more types of host microorganisms, such as *Escherichia coli* and *Bacillus brevis*, various shuttle vectors can be used. Fragments of the vectors can also be obtained by cleaving with the above-mentioned restriction enzymes.

To ligate a DNA fragment to a vector fragment, a known DNA ligase is used. After annealing, a DNA fragment is ligated to a vector fragment so as to construct a recombinant vector.

Hosts used for transformation are not specifically limited so far as they can express the gene of this invention. Examples of the host cells include bacteria belonging to the genera Escherichia, such as *Escherichia coli*, the genera Bacillus, such as *Bacillus subtilis*, and the genera Pseudomonas, such as *Pseudomonas putida*, yeasts such as *Saccharomyces cerevisiae* and *Schizosaccharomyces pombe*, animal cells, such as COS and CHO cells, and insect cells, such as Sf9.

When a bacterium such as *Escherichia coli* is used as a host cell, a preferable recombinant vector can autonomously replicate in the bacterium and comprises a promoter, a ribosome binding sequence, the gene of this invention, and a transcription termination sequence. The recombinant vector may also contain a gene to regulate a promoter.

Examples of Escherichia bacteria include, *E. coli* DH5α and Bacillus bacteria include *Bacillus subtilis*, but not limited thereto.

Any promoter that can be expressed in a host cell may be used. Examples of such a promoter include promoters derived from *Escherichia coli* or phages, such as trp promoter, lac promoter, PL promoter, and PR promoter. Artificially designed and modified promoters, such as tac promoter may also be used.

Any method to introduce recombinant vectors into bacteria, that is, to introduce DNA into bacteria may be used and is not specifically limited. Examples of such methods include a method using calcium ion, electroporation and the like.

When yeast is used as a host cell, *Saccharomyces cerevisiae*, *Schizosaccharomyces pombe* and the like are used. In this case, promoters used herein are not specifically limited so far as they can express in yeast. Examples of such a promoter include gal 1 promoter, gal 10 promoter, heat shock protein promoter, MFα1 promoter, PH05 promoter, PGK promoter, GAP promoter, ADH promoter, and AOX1 promoter.

Methods to introduce recombinant vectors into yeast are not specifically limited. Any method to introduce DNA into yeast may be used. Examples of such methods include electroporation (Becker, D. M. et al., Methods. Enzymol., 194: 182, 1990), spheroplast method (Hinnen, A. et al., Proc. Natl. Acad. Sci., USA, 75, 1929, 1978), lithium acetate method (Itoh, H., J. B acteriol., 153, 163, 1983) and the like.

When an animal cell is used as a host cell, examples of host cells include mouse cells COS-7, Vero, Chinese hamster ovarian cells (CHO cells), mouse L cells, rat GH3, and human FL cells. Examples of promoters include SRα promoter, SV40 promoter, LTR promoter, and CMV promoter. In addition, an initial gene promoter of human cytomegalovirus may also be used. Examples of methods of introducing recombinant vectors into animal cells include electroporation, calcium phosphate transfection and lipofection.

When an insect cell is used as a host cell, Sf9 cells and the like are used. Examples of methods of introducing recombinant vectors into insect cells include calcium phosphate transfection, lipofection, and electroporation.

3. Production of useful substances

A whole or a part of the genes of the present invention, or a whole genomic DNA can be used as basic data for DNA analysis based on a simple metabolic system of Buchnera. For example, analysis made on function of genomic DNA having a nucleotide sequence of SEQ ID NO:1 or function of at least one gene out of genes shown in Table 1 provides genetic information involving the metabolic system. Such genetic information can be used for development of pesticides, which can suppress the growth of Buchnera by inhibiting specifically a part of the metabolic pathway of Buchnera.

Though aphids feed on plant sieve tube fluid, which is deficient in nutrients other than sugar, they have extremely strong fertility. This is because Buchnera supply nutrients (including essential amino acids, vitamin B and other unknown nutrients), which aphids cannot synthesize. Accordingly, the genomic data of Buchnera should contain useful genes encoding the above nutrients. That is, useful substances can be produced by expressing these genes.

Proteins of interest (useful substances) can be obtained in this invention by culturing the aforementioned transformants containing genes of interest and collecting the protein from the culture products. Here the term "culture product" means either culture supernatants, or culture cells or culture bacteria, or disrupted cells or bacteria.

The transformants of this invention are cultured in/on media by normal techniques employed for culturing hosts.

A medium for culturing transformants obtained by using microorganisms including *Escherichia coli*, yeast and the like as hosts contains a carbon source, a nitrogen source, and inorganic salts, which the microorganisms can assimilate, and allows the transformant to grow efficiently. Either natural media or synthetic media can be used if they satisfy the above conditions.

Examples of carbon sources include glucose, fructose, sucrose, and carbohydrates e.g., starch, organic acids e.g., acetic acid and propionic acid, and alcohol e.g., ethanol and propanol. Examples of nitrogen sources include ammonia, salts of inorganic acids or organic acids, e.g., ammonium chloride, ammonium sulfate, ammonium acetate, and ammonium phosphate, other nitrogen-containing compounds, peptone, meat extract, and corn steep liquor. Examples of inorganic substances include potassium primary phosphate, potassium secondary phosphate, magnesium phosphate, magnesium sulfate, sodium chloride, ferrous sulfate, manganese sulfate, copper sulfate, and calcium carbonate.

Culturing is performed by shaking culture or submerged aeration-agitation culture under aerobic conditions at 37° C. for 6 to 24 hours. The pH is kept within a range from 7.0 to 7.5 while culturing. The pH is adjusted using inorganic or organic acid, alkaline solutions or the like.

If necessary, an antibiotics e.g., ampicillin or tetracycline may be added to the media while culturing.

When microorganisms transferred with the expression vectors using inducible promoters are cultured, inducers may be added to the media if necessary. For example, isopropyl-β-D-thiogalactopyranoside (IPTG) or the like may be added to the media when microorganisms transferred with the expression vectors containing lac promoter are cultured; indoleacrylic acid (IAA) or the like may be added when microorganisms transferred with the expression vectors containing trp promoter are cultured.

The media for culturing transformants obtained by using animal cells as host cells include generally used RPMI1640 media, DMEM media, or those to which fetal calf serum or the like is added. Normally, the transformant is cultured in the presence of 5% $CO_2$ for 1 to 30 days at 37° C. If necessary, antibiotics e.g., kanamycin and penicillin may be added to the medium while culturing.

When the protein of interest is produced within a bacterium or a cell, the protein is extracted by disrupting the bacterium or the cell. Further, when the protein of interest is produced outside a bacterium or extracellularly, the culture solution is used as it is or the bacterium or the cell is removed by centrifugation. Then the protein of interest can be isolated and purified from the aforementioned culture product by using appropriate combination of one or more of general biochemical techniques for isolation and purification of proteins, including ammonium sulfate precipitation, gel chromatography, ion exchange chromatography, and affinity chromatography.

Whether the protein of interest is obtained or not can be confirmed by SDS-polyacrylamide gel electrophoresis or the like.

Sequence Listing Free Text

SEQ ID NO:4 Synthetic DNA
SEQ ID NO:5 Synthetic DNA
SEQ ID NO:6 Synthetic DNA
SEQ ID NO:7 Synthetic DNA

EXAMPLE

Figure 1:
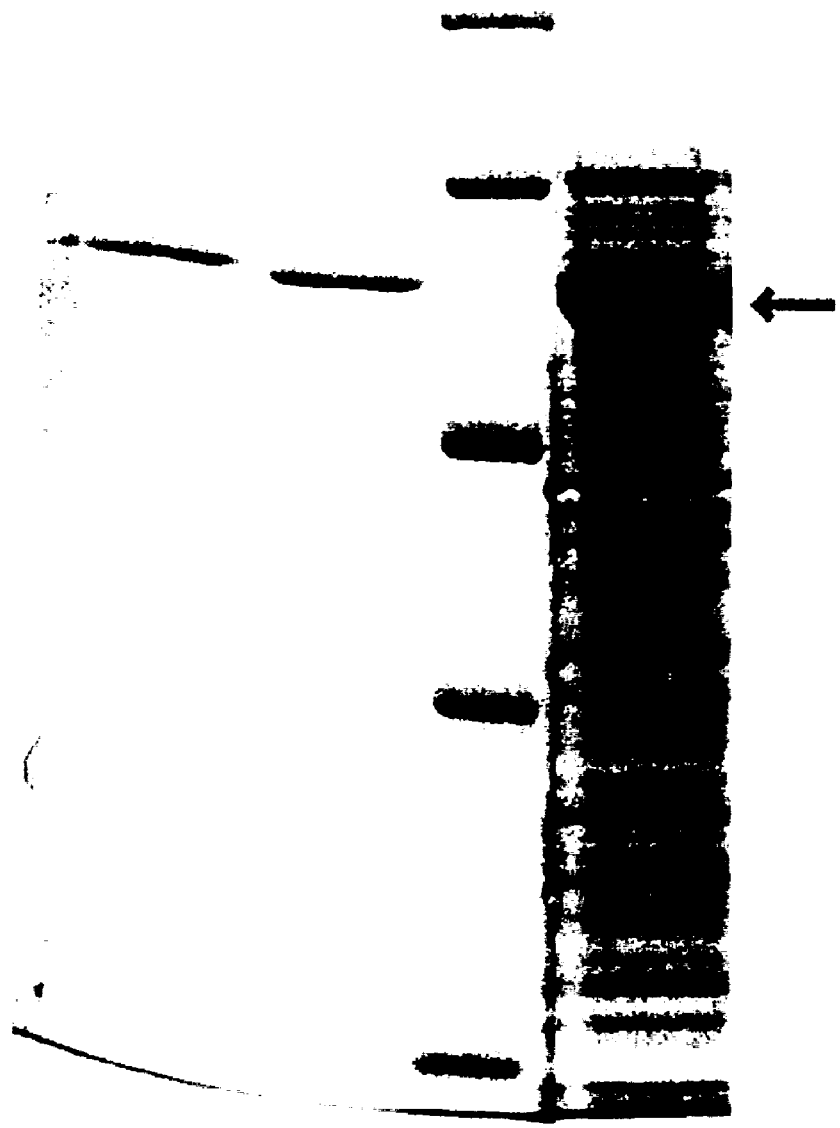
FIG. 1 is a photograph of SDS-polyacrylamide gel electrophoresis showing the purification results of DnaK protein.

The invention will now be described by way of examples, but the technical scope of this invention shall not be limited by the examples.

Example 1

Genomic DNA of Buchnera sp.

(1) Isolation of Buchenra cells from aphids

*Acyrthosiphon pisum* (Harris) was dissected in buffer A (35 mM Tris-HCl (pH 7.5) 25 mM KCl, 10 mM $MgCl_2$, 250 mM sucrose) and the bacteriocytes were collected. The bacteriocytes were crushed by pipetting in buffer A and subjected to filtration through 5 μm pore size filter (Millipore corporation), thereby isolating Buchnera cells.

(2) Whole genome shotgun sequencing

Genomic DNA was isolated and prepared by a standard phenol/chloroform protocol.

Next, the sequence of the genomic DNA was determined by the whole genome shotgun sequencing. This method is same as that of Fleischmann et al., (Fleischmann, R. D. et al. Whole-genome random sequencing and assembly of Haemophilus influenzae Rd. Science 269, 496–512, 1995) except that some modifications were made (Partial fill-in method was employed) to avoid chimera formation upon the construction of libraries.

The isolated genomic DNA 15 μg was treated with SauAI 2U in 120 μl of reaction solution for 40 minutes at 37° C. resulting in limited digestion of the genomic DNA. The product was subjected to electrophoresis, and portions corresponding to 1.5 to 6 kb were cut out together with agarose gel, and DNAs were purified using a GENECLEAN kit (BIO101). The fragment digested with Sau3AI has a GATC overhang end at the 5' end. These fragments are treated with Klenow enzyme (Takara) in the presence of dGTP and dATP for 15 minutes at 37° C. so that A and G bases are polymerized to form 5'-overhang with GA. Such a method in which the bases of an overhang end are partially polymerized is called Partial fill-in method. A cloning vector used herein was pSFI-CV1. For more information on the Partial fill-in method and the vector pSFI-CV1, please refer to Hattori et al's paper (Hattori, M. et al. A novel method for making nested deletions and its application for sequencing of a 300 kb region of human APP locus. Nucleic Acids Res. 25, 1802–1808, 1997).

This vector was treated with SalI restriction enzyme for 2 hours at 37° C. After ethanol precipitation, the product was treated by the Partial fill-in method. The SalI fragment has an AGCT overhang end at the 3' end. Treatment of the SalI fragment in the presence of dTTP and dCTP results in the formation of CT end. Hence it becomes complementary to the terminal of the pretreated genomic DNA fragment so as to make ligation possible and avoid chimera formation. The products were treated with a DNA ligation kit ver. 2 (Takara) for 18 hours at 15° C., so that the genomic fragments were inserted into the vectors. The products were transformed into *Escherichia coli* DH5α competent cells (Takara). The ampicillin-resistant colonies were picked up and subjected to PCR to confirm that the genomic DNA fragments had been directly inserted. Primers used herein are as follows.

LR: 5'-TCCGGCTCGTATGTTGTGTGGA-3'   (SEQ ID NO:4)

LL: 5'-GTGCTGCAAGGCGATTAAGTTGG-3'  (SEQ ID NO:5)

PCR was performed for 30 cycles of 96° C. for 15 seconds and 68° C. for 3 minutes followed by one cycle at 70° C. for 10 minutes in the following reaction composition.

| | |
|---|---|
| 10× buffer | 2.5 µl |
| 2.5 mM dNTP | 2.5 µl |
| Primer LR (3.2 pmol) | 0.25 µl |
| Primer LL (3.2 pmol) | 0.25 µl |
| Takara ExTaq | 0.1 µl |
| Total | 25 µl |

The resulting PCR products were treated with alkaline phosphatase/exonuclease using a PCR product pre-sequencing kit (Amersham LIFE SCIENCE) and used as templates for sequencing. Sequencing reaction was performed using a commercial kit (ABI PRISM BigDye™ Terminator cycle sequencing Kits, dRhodoamine Terminator cycle sequencing kit, BigDye™ Primer Cycle Sequencing Kits, PE Biosystems) according to the manufacturer's protocols. Sequencing primers used herein were M13 forward or reverse primers. Sequencing was performed using ABI 377DNA sequencer (PE Biosystems). To determine a whole nucleotide sequence of Buchnera genome, approximately 10,000 sequencing reactions were needed. The sequence data from approximately 10,000 DNA fragments were reconstructed (by aligning, overlapping and connecting sequence fragments) on the UNIX workstation using phred, phrap, and consed computer programs (University of Washington).

The plasmid DNA of this invention can also be isolated and its nucleotide sequence can be determined in the same manner as employed for the genomic DNA by the whole genome shotgun sequencing.

(3) Identification of genes

Two strategies were used to identify regions encoding proteins based on the genome sequence data. In one strategy employing ORF prediction program, Gene Hacker program (Yada, RIKEN) was used. In the other strategy employing a method to predict ORF from sequence homology, NCBI BLAST program was used. The results from the two strategies were compared and the nucleotide sequence represented by SEQ ID NO:1 was finally determined. Further, 572 regions for encoding proteins (CDS) in the sequence represented by SEQ ID NO:1 were identified (Table 1).

(4) Identification of plasmids

The nucleotide sequences of two plasmids were determined in the same manner as for determining the nucleotide sequence of the genomic DNA. The two plasmids were leucine and tryptophan plasmids. The isolated nucleotide sequence of the leucine plasmid is as shown in SEQ ID NO:2; that of the tryptophan plasmid in SEQ ID NO:3. These plasmids can autonomously replicate within Buchnera and the amount of amplification is several times greater than that of chromosomal genome. Furthermore, these plasmids contain genes involved in the metabolism of essential amino acids (Table 2). Hence, the plasmids of this invention is useful in gene therapy designed to supply amino acids by introducing the plasmids into patients suffered from amino acid metabolic disorder due to failure of function or hypofunction of such a gene.

Number of regions for encoding proteins and number of RNA of the genomic DNA and plasmids above are as follows.

| | Regions for encoding protein | RNA | Total |
|---|---|---|---|
| Chromosome | 572 | 36 | 608 |
| Plasmid | 11 | 0 | 11 |

Example 2

Excessive Expression and Purification of DnaK Protein

A gene dnaK encoding DnaK protein (see BU153 in Table 1) was amplified by PCR, treated with restriction enzymes EcoRI and SalI for 2 hours at 37° C., and then integrated into EcoRI/SalI sites of pUC18 vector. PCR was performed using reaction solution having the following composition for 30 cycles, each cycle consisting of denaturation for 5 minutes at 96° C., annealing for 1 minute at 50° C., and extension for 4 minutes at 72° C. Primers used herein are as follows.

(SEQ ID NO:6)
Primer F: 5'-ATCGAATTCTAAATAGGAGAAACTTTAATGGGTA-3'

(SEQ ID NO:7)
Primer R: 5'-CTAGTCGACGTTCAATGATTCG-3'

| | |
|---|---|
| Genomic DNA | 0.625 µl |
| | (300 ng) |
| 10× buffer | 2.5 µl |
| 2.5 mM dNTP | 2.5 µl |
| Primer F (100 pmol) | 0.5 µl |
| Primer R (100 pmol) | 0.5 µl |
| Takara ExTaq | 0.125 µl |
| Total | 25 µl |

The resulting product was transformed into *Escherichia coli* by electroporation, and allowed to express excessively in *E. coli*. *E.coli* was disrupted by lisozyme and ultrasonication. Soluble proteins were collected by gelatin affinity chromatography, thereby obtaining DnaK protein. Since DnaK of the host *E.coli* was also contained at this stage, native-PAGE-applied disc preparative electrophoresis was performed (Nihon Eido). This electrophoresis notices that DnaK protein of *E.coli* and of Buchnera are similar in the primary structure, but significantly differ in the isoelectric point (Buchnera has a higher isoelectric point than that of *E.coli*). It can also be applied for purification of other proteins in addition to DnaK.

Therefore, DnaK protein of interest was isolated and purified by separating from that derived from *E.coli* (FIG. 1, a band pointed by an arrow in lane 1).

In FIG. 1, each lane is as follows.

Lane 1: Purified Buchnera DnaK

Lane 2: *E.coli* DnaK

Lane 3: Molecular weight marker

Lane 4: *E.coli* extract after excessive expression (In FIG. 1, lane 1 is the protein of interest)

The present invention provides Buchnera genomic DNA. DNA of this invention is useful as genetic information to develop agricultural chemicals for destroying aphids and to analyze the metabolic mechanism of aphids. Moreover, DNA of this invention can be used as genetic information or raw materials for synthesis of useful substances.

All the publications, patents and patent applications cited in the present specification are incorporated herein by reference in their entireties.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6632935B2). An electronic copy of the "Sequence Listing" will also be available from the USPTO upon request and payment of the fee set forth in 37 CFR 1.19(b)(3).

What is claimed is:

1. An isolated and preferred genome DNA of Buchnera sp., having a nucleotide sequence represented by SEQ ID NO:1.

* * * * *